United States Patent [19]

Rajadhyaksha

[11] Patent Number: 4,876,249

[45] Date of Patent: Oct. 24, 1989

[54] COMPOSITIONS AND METHOD COMPRISING HETEROCYCLIC COMPOUNDS CONTAINING TWO HETEROATOMS

[76] Inventor: Vithal J. Rajadhyaksha, 27436 Esquina, Mission Viejo, Calif. 92691

[21] Appl. No.: 2,387

[22] Filed: Jan. 12, 1987

[51] Int. Cl.⁴ .............................................. A61K 31/58
[52] U.S. Cl. .................................................... 514/174
[58] Field of Search .......................................... 514/174

[56] References Cited

U.S. PATENT DOCUMENTS 4,282,216  8/1981  Rovee et al. ......................... 514/174
4,473,565  9/1984  Rovee et al. ......................... 514/174

Primary Examiner—Stanley J. Friedman
Attorney, Agent, or Firm—Grant L. Hubbard

[57] ABSTRACT

A method and compositions for topically administering physiologically active agents through the skin and mucous membranes of humans and animals in a transdermal device or formulation for systemic use or to the skin of humans and animals for localized use comprising applying to such skin or membrane a mixture of said physiologically active agent and a non-toxic, effective penetrating amount of penetration enhancing compound having the structural formula I:

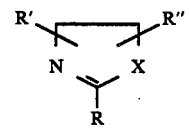

wherein: R is a saturated or unsaturated hydrocarbon group with from 5 to 19 carbon atoms; R' and R" are hydrogen, lower alkyl, trifluoromethyl, lower hydroxyalkyl or lower alkyl ester of lower hydroxyalkyl, with the proviso that both R' and R" are not lower hydroxyalkyl; X is O or $NR_1$; $R_1$ being hydrogen, lower alkyl, lower alkenyl, lower hydroxyalkyl or lower alkyl ester of lower hydroxyalkyl are disclosed.

11 Claims, No Drawings

COMPOSITIONS AND METHOD COMPRISING HETEROCYCLIC COMPOUNDS CONTAINING TWO HETEROATOMS

BACKGROUND OF THE INVENTION

Many physiologically active agents are best applied topically to obtain desirable results. Topical application, in the form of creams, lotions, gels, solutions, etc., largely avoids side effects of the agents and permits high level concentrations of the agents.

Some therapeutic drugs may also be administered for systemic use through the skin or other body membranes including intranasal and intravaginal application of humans and other animals, utilizing a transdermal device or formulated in a suppository or aerosol spray. For some years, pharmaceutical researchers have sought an effective means of introducing drugs into the bloodstream by applying them to the unbroken skin. Among other advantages, such administration can provide a comfortable, convenient and safe way of giving many drugs now taken orally or infused into veins or injected intramuscularly.

Using skin as the portal for drug entry offers unique potential, because transdermal delivery permits close control over drug absorption. For example, it avoids factors that can cause unpredictable absorption from gastrointestinal tract, including: changes in acidity, motility, and food content. It also avoids initial metabolism of the drug by the liver known as the first pass effect. Thus, controlled drug entry through skin can achieve a high degree of control over blood concentrations of drug.

Close control over drug concentration in blood can translate readily into safer and more comfortable treatment. When a drug's adverse effects occur at higher concentrations than its beneficial ones, rate control can maintain the concentration that evoke only or principally the drug's desired actions. This ability to lessen undesired drug actions can greatly reduce the toxicity hazards that now restrict or prevent the use of many valuable agents.

Transdermal delivery particularly benefits patients with chronic disease. Many such patients have difficulty following regimens requiring several doses daily of medications that repeatedly cause unpleasant symptoms. They find the same drugs much more acceptable when administered in transdermal system that require application infrequently —in some cases, only once or twice weekly —and reduce adverse effects.

Transdermal delivery is feasible for drugs effective in amounts that can pass through the skin area and that are substantially free of localized irritating or allergic effects. While these limitations may exclude some agents, many others remain eligible for transdermal delivery. Moreover, their numbers will expand as pharmaceutical agents of greater potency are developed. Particularly suitable for transdermal delivery are potent drugs with only a narrow spread between their toxic and safe blood concentrations, those having gastrointestinal absorption problems, those susceptible to a higher first pass liver metabolism or those requiring frequent dosing in oral or injectable form.

Transdermal therapy permits much wider use of natural substances such as hormones. Often the survival times of these substances in the body are so short that they would have to be taken many times daily in ordinary dosage forms. Continuous transdermal delivery provides a practical way of giving them, and one that can mimic the body's own patterns of secretion.

At present, controlled transdermal therapy appears feasible for many drugs used for a wide variety of ailments including, but not limited to, circulatory problems, hormone deficiency, respiratory ailments, and pain relief.

Percutaneous administration can have the advantage of permitting continuous administration of drug to the circulation over prolonged periods of time to obtain a uniform delivery rate and blood level of drug. Commencement and termination of drug therapy are initiated by the application and removal of the dosing devices from the skin. Uncertainties of administration through the gastrointestinal tract and the inconvenience of administration by injection are eliminated. Since a high concentration of drug never enters the body, problems of pulse entry are overcome and metabolic half-life is not a factor of controlling importance.

The greatest problems in applying physiologically active agents topically or transdermally is that the skin is an effective barrier to penetration. The epidermis of the skin has an exterior layer of dead cells called the stratum corneum which is tightly compacted and oily and which provides an effective barrier against gaseous, solid or liquid chemical agents, whether used alone or in water or in oil solutions. If a physiologically active agent penetrates the stratum corneum, it can readily pass through the basal layer of the epidermis and into the dermis.

Although the effectiveness of the stratum corneum as a barrier provides great protection, it also frustrates efforts to apply beneficial agents directly to local areas of the body. The inability of physiologically active agents to penetrate the stratum corneum prevents their effective use of treating such conditions as inflammation, acne, psoriasis, herpes labialis, herpes genitalis, eczema, infections caused by fungi, viruses and other microorganisms, or other disorders or conditions of the skin or mucous membranes or of conditions beneath the exterior surface of the skin or mucous membranes. The stratum corneum also prevents the skin from absorbing and remaining cosmetic-type materials such as sunscreens, perfumes, mosquito repellents and the like.

Physiologically active agents may be applied to the locally affected parts of the body in the form of a solution, cream, lotion or gel utilizing the vehicle system described herein. These agents may also be delivered for systemic use utilizing the vehicle system in a transdermal patch. Vehicles such as USP cold cream, ethanol and various ointments, oils, solvents and emulsions have been used heretofore to apply physiologically active ingredients locally. Most such vehicles are not effective to carry significant amounts of physiologically active agents into and through the skin. One such vehicle is dimethyl sulfoxide, which is described in U.S. Pat. No. 3,551,554.

My previous inventions disclosed in U.S. Pat. Nos. 3,989,816; 3,991,203; 4,112,170; 4,316,893; 4,415,563; 4,423,040; 4,424,210; 4,444,762 describe a method for enhancing the topical administration of physiologically active agents by combining such an agent with an effective amount of a penetration enhancer and applying the combination topically to humans or animals, in the form of solution, cream, gel, lotion etc. This prior art discloses N-alkyl substituted cyclic lactams as penetration enhancers.

My related U.S. Pat. No. 4,405,616 describes a method for administering systemically active agents through the skin or other body membranes of humans and animals, utilizing a transdermal device or formulation containing an effective amount of a suitable membrane penetration enhancer selected from the disclosed N-alkyl substituted cyclic lactams.

My related U.S. application, Ser. No. 783,621, filed on Sept. 30, 1985, describes a method for enhancing topical and transdermal administration of physiologically active agents with membrane penetration enhancers selected from the alkanoic acid cyclic amides disclosed therein.

Penetration enhancers for enhancing systemic administration of therapeutic agents transdermally disclosed in the art include dodecyl pyrrolidone, dimethyl lauramide and dimethyl sulfoxide. These agents may be used prior to or concurrently with administration of the active agent, see, e.g., U.S. Pat. Nos. 4,031,894; 3,996,934 and 3,921,636.

SUMMARY OF THE INVENTION

The invention relates to compositions for carrying physiologically active agents through body membranes such as skin and for retaining these agents in the body tissues and further relates to a method of administering systemically active agents through the skin or other body membranes of humans and animals, utilizing a transdermal device or formulation, containing an effective, non-toxic amount of a membrane penetration enhancer having the structural formula I:

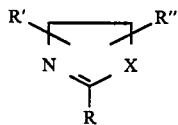

wherein:
R is a saturated or unsaturated hydrocarbon group with from 5 to 19 carbon atoms,
R' and R" are hydrogen, lower alkyl, trifluoromethyl, lower hydroxyalkyl or lower alkyl ester of lower hydroxyalkyl, with the proviso that both R' and R" are not lower hydroxyalkyl,
X is O or $NR_1$; $R_1$ being Hydrogen, lower alkyl, lower alkenyl, lower hydroxyalkyl or lower alkyl ester of lower hydroxyalkyl.

In one preferred embodiment of I, R' and R" are H; R, X and $R_1$ being as defined. The preferred compounds of this embodiment are:
2-(2-dodecyl)-2-oxazoline,
2-(2-methyl-2-decyl)-2-oxazoline,
2-Undecyl-2-imidazoline,
1-Methyl-2-heptyl-2-imidazoline,
1-Isopropyl-2-undecyl-2-imidazoline,
1-Hydroxyethyl-2-octyl-2-imidazoline, and
1-[2-(Trimethylacetoxy)ethyl]-2-imidazoline.

In another preferred embodiment of the composition I, R' is Hydrogen, R" is lower alkyl or trifluoromethyl; X and $R_1$ being as defined. The preferred compounds of this embodiment are:
4-Methyl-2-(2-dodecyl)-2-oxazoline,
4-Isopropyl-2-(2-dodecyl)-2-oxazoline,
4-Trifluoromethyl-2-(2-dodecyl)-2-oxazoline,
4-Isopropyl-2-(2-methyl-2-decyl)-2-oxazoline,
4-Methyl-2-undecyl-2-imidazoline,
4-Isopropyl-2-undecyl-2-imidazoline,
4-t-Butyl-2-undecyl-2-imidazoline,
4-Trifluoromethyl-2-undecyl-2-imidazoline,
1,4-Diisopropyl-2-undecyl-2-imidazoline,
4-Methyl-1-isopropyl-2-undecyl-2-imidazoline,
4-Methyl-2-(2-dodecyl)-2-imidazoline, and
4-Methyl-2-(2-methyl-2-decyl)-2-imidazoline.

In yet another preferred embodiment of I, R' and R" are lower alkyl or trifluoromethyl; R and X being as defined. The preferred compounds of this embodiment are:
4,4-Dimethyl-2-undecyl-2-oxazoline,
4-Methyl-4-trifluoromethyl-2-undecyl-2-oxazoline,
4,4-Dimethyl-2-(1-dodecen-2-yl)-2-oxazoline,
4-Methyl-4-trifluoromethyl-2-(1-dodecen-2-yl)-2oxazoline,
4,4-Dimethyl-2-(2-dodecyl)-2-oxazoline,
4,4-Dimethyl-2-(2-methyl-2-decyl)-2-oxazoline,
4,4-Dimethyl-2-undecyl-2-imidazoline,
4-Methyl-4-t-butyl-2-undecyl-2-imidazoline,
4,4-Dimethyl-1-isopropyl-2-undecyl-2-imidazoline,
4-Methyl-1,4-diisopropyl-2-undecyl-2-imidazoline,
4,4-Dimethyl-2-(2-dodecyl)-2-imidazoline,
4,4-Dimethyl-1-isopropyl-2-(2-dodecyl)-2-imidazoline,
4,4-Dimethyl-2-(2-methyl-2-decyl)-2-imidazoline,
4,4-Dimethyl-1-isopropyl-2-(2-methyl-2-decyl)-2imidazoline.

In still another preferred embodiment of I, R' is lower alkyl or trifluoromethyl and X is O; the other substituents being as defined.
The preferred compounds are:
4-Hydroxymethyl-4-methyl-2-undecyl-2-oxazoline,
4-Hydroxymethyl-4-trifluoromethyl-2-undecyl-2-oxazoline,
4-Trimethylacetoxymethyl-4-methyl-2-undecyl-2-oxazoline,
4-Hydroxymethyl-4-methyl-2-(2-dodecyl)-2-oxazoline,
4-Hydroxymethyl-4-methyl-2-(2-methyl-2-decyl)-2oxazoline,
4-Trimethylacetoxymethyl-4-methyl-2-(2-dodecyl)-2oxazoline, and
4-Trimethylacetoxymethyl-4-methyl-2-(2-methyl-2-decyl)-2-oxazoline.

It has been found that the physiologically active agents are carried through body membranes by the claimed penetration enhancers and are retained in the body tissue when applied topically in form of a creme, gel, or lotion or absorbed systemically when applied in the form of a transdermal device or formulation, for example, as a transdermal patch, a rectal or vagina suppository, as a nasal spray or when incorporated in a vaginal sponge or tampon.

DETAILED DESCRIPTION OF THE INVENTION

Typical examples of compounds included in the foregoing formula I of this invention are the following:
1. 4-Trifluoromethyl-2-undecyl-2-oxazoline.
2. 4-Isopropyl-2-nonyl-2-oxazoline.
3. 4-Isopropyl-2-undecyl-2-oxazoline.
4. 4-t-Butyl-2-undecyl-2-oxazoline.
5. 4-Methyl-4-trifluoromethyl-2-undecyl-2-oxazoline.
6. 4-Methyl-4-isopropyl-2-undecyl-2-oxazoline.
7. 4-Methyl-4-t-butyl-2-undecyl-2-oxazoline.
8. 4-Trifluoromethyl-2-(1-dodecen-2-yl)-2-oxazoline.
9. 4,4-Dimethyl-2-(1-dodecen-2-yl)-2-oxazoline.
10. 4-methyl-4-trifluoromethyl-2-(1-dodecen-2-yl) -2-oxazoline.

11. 4-Hydroxymethyl-4-trifluoromethyl-2-undecyl-2-oxazoline.
12. 4-Trimethylacetoxymethyl-4-methyl-2-undecyl-2-oxazoline.
13. 2-(2-decyl)-2-oxazoline.
14. 2-(2-dodecyl)-2-oxazoline.
15. 4-Methyl-2-(2-dodecyl)-2-oxazoline.
16. 4-Isopropyl-2-(2-dodecyl)-2-oxazoline.
17. 4-t-Butyl-2-(2-dodecyl)-2-oxazoline.
18. 4-Trifluoromethyl-2-(2-dodecyl)-2-oxazoline.
19. 4,4-Dimethyl-2-(2-dodecyl)-2-oxazoline.
20. 4-Methyl-4-isopropyl-2-(2-dodecyl)-2-oxazoline.
21. 4-Methyl-4-t-butyl-2-(2-dodecyl)-2-oxazoline.
22. 4-Methyl-4-trifluoromethyl-2-(2-dodecyl)-2 oxazoline.
23. 4-Hydroxymethyl-4-methyl-2-(2-dodecyl)-2oxazoline.
24. 4-[2-(Trimethylacetoxy)ethyl]-4-methyl-2(2-dodecyl)-2-oxazoline.
25. 2-(2-methyl-2-decyl)-2-oxazoline.
26. 2-(2-methyl-2-dodecyl)2-oxazoline.
27. 4-Trifluoromethyl-2-(2-methyl-2-decyl)-2oxazoline.
28. 4,4-Dimethyl-2-(2-methyl-2-decyl)-2-oxazoline.
29. 4,4-Dimethyl-2-(2-methyl-3-tridecyl)-2-oxazoline.
30. 2-Nonyl-2-imidazoline.
31. 2-Undecyl-2-imidazoline.
32. 2-Tridecyl-2-imidazoline.
33. 1-Isopropyl-2-pentyl-2-imidazoline.
34. 1-Methyl-2-heptyl-2-imidazoline.
35. 1-Methyl-2-undecyl-2-imidazoline.
36. 1-Hydroxyethyl-2-octyl-2-imidazoline.
37. 1-[2-(Trimethylacetoxy)ethyl]-2-octyl-2imidazoline.
38. 1-Isopropyl-2-undecyl-2-imidazoline.
39. 4-Methyl-2-undecyl-2-imidazoline.
40. 4-Isopropyl-2-undecyl-2-imidazoline.
41. 4-t-Butyl-2-undecyl-2-imidazoline.
42. 4-Trifluoromethyl-2-undecyl-2-imidazoline.
43. 1,4-Diisopropyl-2-undecyl-2-imidazoline.
44. 4-t-Butyl-1-isopropyl-2-undecyl-2-imidazoline.
45. 4,4-Dimethyl-2-nonyl-2-imidazoline.
46. 4,4-Dimethyl-2-undecyl-2-imidazoline.
47. 4-Methyl-4-isopropyl-2-undecyl-2-imidazoline.
48. 4-Methyl-4-t-butyl-2-undecyl-2-imidazoline.
49. 4,4-Diisopropyl-2-undecyl-2-imidazoline.
50. 4-Methyl-4-trifluoromethyl-2-undecyl-2-imidazoline.
51. 4,4-Dimethyl-1-isopropyl-2-pentyl-2-imidazoline.
52. 4,4-Dimethyl-1-isopropyl-2-undecyl-2-imidazoline.
53. 4,4-Dimethyl-1-isopropyl-2-tridecyl-2-imidazoline.
54. 4,4-Dimethyl-1-isopropyl-2-pentadecyl-2-imidazoline.
55. 4,4-Dimethyl-1-isopropyl-2-heptadecyl-2-imidazoline.
56. 4,4-Dimethyl-1-n-butyl-2-heptadecyl-2-imidazoline.
57. 4,4-Dimethyl-1-s-butyl-2-heptadecyl-2-imidazoline.
58. 4-Methyl-1,4-diisopropyl-2-undecyl-2-imidazoline.
59. 4-Methyl-4-t-butyl-1-isopropyl-2-undecyl-imidazoline.
60. 1,4,4-Triisopropyl-2-undecyl-2-imidazoline.
61. 4,4-Dimethyl-1-hydroxyethyl-2-undecyl-2imidazoline.
62. 4,4-Dimethyl-1-hydroxyethyl-2-heptadecyl-2-imidazoline.
63. 4,4-Dimethyl-1-[2-(Trimethylacetoxy)ethyl]-2undecyl-2-imidazoline.
64. 4,4-Di8;ethyl-1-(1-hydroxy-2-methyl-2-propyl)-2-undecyl-2-imidazoline.
65. 4,4-Dimethyl-1-(1-acetoxy-2-methyl-2-propyl) -2-undecyl-2-imidazoline:
66. 2-(2-decyl)-2-imidazoline.
67. 2-(2-dodecyl)-2-imidazoline.
68. 1-Hydroxyethyl-2-(2-dodecyl)-2-imidazoline.
69. 1-[2-(Trimethylacetoxy)ethyl]-2-(2-dodecyl) -2-imidazoline.
70. 1-Isopropyl-2-(2-dodecyl)-2-imidazoline.
71. 4,4-Dimethyl-2-(2-dodecyl)-2-imidazoline.
72. 4,4-Dimethyl-1-isopropyl-2-(2-dodecyl)-2imidazoline.
73. 2-(1-Dodecen-2-yl)-2-imidazoline.
74. 1-Isopropyl-2-(1-dodecen-2-yl)-2-imidazoline.
75. 4,4-Dimethyl-2-(1-dodecen-2-yl)-2-imidazoline.
76. 4,4-Dimethyl-1-isopropyl-2-(1-dodecen-2-yl) -2-imidazoline.
77. 2-(2-methyl-2-decyl)-2-imidazoline.
78. 2-(2-methyl-2-dodecyl)-2-imidazoline.
79. 1-Hydroxyethyl-2-(2-methyl-2-decyl)-2imidazoline.
80. 1-Trimethylacetoxyethyl-2-(2-methyl-2-decyl)-2-imidazoline.
81. 4,4-Dimethyl-2-(2-methyl-2-decyl)-2-imidazoline.
82. 4,4-Dimethyl-1-isopropyl-2-(2-methyl-2-decyl)-2-imidazoline.
83. 4,4-Dimethyl-1-hydroxyethyl-2 (2-methyl-2decyl)-2-imidazoline.
84. 4,4-Dimethyl-1-[2-(Trimethylacetoxy)ethyl]-2(2-methyl-2-decyl)-2-imidazoline.
85. 4,4-Dimethyl-1-(1-hydroxy-2-methyl-2-propyl)-2-undecyl-2-imidazoline.

The following compounds are less stable and, hence, less desirable for most applications; however, where stability is not paramount or can be achieved or instability overcome through packaging, increased concentration, particular derivatives or formulations, these compounds may be useful:
86. 4-Methyl-2-nonyl-2-oxazoline.
87. 4-Methyl-2-undecyl-2-oxazoline.
88. 4,4-Dimethyl-2-nonyl-2-oxazoline.
89. 4,4-Dimethyl-2-undecyl-2-oxazoline.
90. 4,4-Dimethyl-2-tridecyl-2-oxazoline.
91. 4-Hydroxymethyl-4-methyl-2-nonyl-2-oxazoline.
92. 4-Hydroxymethyl-4-methyl-2-undecyl-2-oxazoline.
93. 4-Hydroxymethyl-4-ethyl-2-undecyl-2-oxazoline.

Another group of compounds have satisfactory penetration enhancing characteristics and may for some limited purposes be regarded as equivalents; however, these compounds are insufficiently stable for most applications and in most formulations. This group of compounds includes:
94. 2-Pentyl-2-oxazoline.
95. 2-Heptyl-2-oxazoline.
96. 2-Nonyl-2-oxazoline.
97. 2-Undecyl-2-oxazoline.
98. 2-Tridecyl-2-oxazoline.
99. 2-pentadecyl-2-oxazoline.
100. 2-Heptadecyl-2-oxazoline. The following 2-oxazolines, encompassed by general formula I of this invention are known in the literature. Compounds 89, 91 and 92 were evaluated for phytotoxicity [Allen and Skoog, Plant Physiol. 26, 611 (1951); C.A. 9790f (1951)]; Compounds 95–100 were evaluated for surface activity [Ishii et al., Yukagaku 7, 70–74(1958); C.A. 55:5993d (1961)]; Compounds 95 and 97 were used to prepare nitrogen containing polymers useful as adhesive and thickeners for water base paints [Litt et al., U.S. Pat. No. 3,483,141, Dec. 9, 1969]; Method of preparation for compounds 94, 95, 97 and 100 is disclosed by Litt et al., U.S. Pat. No. 3,562,263, Feb. 9, 1971; by Bassiri et al., Polymer Lett. 5,871-9 (1967) and by Levy and Litt, Polymer Lett. 5,881-6 (1967) and for compound 97 by Seeliger and Thier, Justus Liebigs Ann. Chem 698, 158–66 (1966); C.A. 66: 37856x (1967) and by Seeliger et al., Angew. Chem., Int. Ed. Engl.5, 875-88(1966); Lactate, citrate and tartrate salts of compounds 88–90 were evaluated for their emulsifying and foaming properties [Kimura et al., Yukagaku, 21, 197–200 (1972); C.A. 77: 50538s (1972)]and same salts of compounds 91, 92 and their $C_{13}$, $C_{15}$, and $C_{17}$ homologs were evaluated for surface activity [Kimura et al., Kogyo Kagaku Zasshi, 63,582-5(1960); C.A.: 58, 11583b (1963); Method of preparation for compound 99 disclosed by Litt et al. in U.S. Pat. No. 3,681,333, Aug. 1, 1972 and compound 99 in a related U.S. Pat. No. 3,681,329 Aug. 1, 1972; Method of preparation for compounds 94, 97 and 100 is disclosed by Witte and Seeliger, Angew. Chem., Int. Ed. Engl. 11,287-8 (1972) and Liebigs Ann. Chem. 996–1009 (1974); Compounds 88–90 and their $C_5$, $C_7$, $C_{15}$ and $C_{17}$ analogs are disclosed as emulsifiers in polymerization of styrene and butadiene [Frump, U.S. Pat. No. 3,886,128; May 27, 1975; C.A. 83: 180219y (1975)]; Organic acid salts of compounds 96–98 were evaluated for their emulsifying and foaming properties [Kimura et al., Yukagaku, 24,869-73 (1975); C.A. 84: 137589c (1976)]; compounds 88–90 and their C5, C7, and C15 analogs were disclosed and compound 88 was evaluated for antimicrobial activity [Hunsucker, U.S. Pat. No. 4,049,819, Sept. 20, 1977; C.A. 87: 195540c (1977)]; Compound 89 and its $C_5$ and $C_{17}$ analogs are disclosed as intermediates in the synthesis of monoacyl glycerols [Hersloef and Gronowitz, Chem. Scr. 22, 230-5 (1983); C.A. 100: 156203n (1984)]; Erskine and Lydon disclose oxazolines with alkyl groups of 7–19 carbon atoms in 2-position and additionally substituted with alkyl or hydroxyalkyl groups with 1–3 carbon atoms in 4 and/or 5 position as surfactants in Iron Blue Pigment Composition suitable for incorporating in transfer or carbon paper inks (U.S. Pat. No. 2,893,886, July 7, 1959); Thompson et al. disclose 2-alkyl-4,4-dimethyl-2$ oxazoline salts of lauryl or oleyl phosphoric acid partial esters as antistatic agents in lubricating compositions for textiles (U.S. Pat. No. 2,976,186, Mar. 21, 1961); Johnson discloses 2-alkyl substituted oxazolines (7–17 carbon atoms), additionally substituted with alkyl or hydroxymethyl groups in 4 position as antifoaming and emulsifying agents in fermentation processes (U.S. Pat. No. 2,443,825, June 22, 1948) and finally compounds 88–90, 9 and analogs are mentioned as intermediates in the synthesis of alpha-substituted acrylic acids [Serota et al., J. Org. Chem 46, 4147-4151 (1981)].

The following 2-imidazoline derivatives, encompassed by general formula I of this invention, are known in the literature. Synthesis of compounds 30, 31 and 32, and other lower alkyl analogs is reported by Morrill (U.S. Pat. No. 2,508,415, May 23, 1950); Compounds 30 and 31 were prepared in low yield by Clintwood and Emmet-Ried, J.Amer.Chem.Soc. 57,2424, (1953); Compound 31 and its $C_{17}$ homolog were synthesized by Waldmann and Chwala, Chem.Ber. 74,1763 (1941); French Pat. No. 811,423, April 14, 1937; U.S. Pat. No. 2,155,877, April 25, 1939; Compound 31 was prepared by Piskov et al; Khim. Geterotsikl, Soedin., 1112 (1976); C.A. 86,5372h (1977); Bockmuhl and Knoll reported the synthesis of $C_{15}$ and $C_{17}$ substituted 2-imidazolines intended to be useful for therapeutic or technical purposes, U.S. Pat. No. 1,958,529, May 15, 1934; C.A. 28,4539 (1934); Wellman and McCallan have reported 2-heptadecyl-2-imdazoline useful as foliage fungicide; C.A. 40,4470 (1946); Kyrides et al., J.Org.Chem. 12,577 (1947) and Shepard and Shonle, J.Amer.Chem.Soc. 69,2269 (1947) have reported synthesis of compounds 31, 32, 34, 35, and 1-ethyl and 1-pentyl-2-undecyl-2-imidazolines in low to moderate yields and their bacteriostatic and local anesthetic activity; Mikeska in U.S. Pat. No. 2,361,488; C.A. 39,2190 (1945) discloses 2-imidazolines substituted in 2-position with saturated or unsaturated alkyl group with 10-23 carbon atoms in paving composition; Russell describes the use of 2-imidazolines and specifically claims 2-heptadecyl-2-imidazoline in herbicidal composition, U.S. Pat. No. 2.514,341, July 4, 1950; Compound 51 was prepared by Harnsberger and Riebsomer, J. Hetero. Chem. 1,188 (1964) and Compounds 51-57 were reported in very low yield by Riebsomer, J.Amer.Chem.Soc. 70,1629 (1948); Compound 31 and its $C_5$, $C_{10}$, $C_{12}$ and $C_{17}$ analogs as well as compound 39 and its $C_{17}$ analog were prepared by Sawa, Nippon Kagaku Zasshi, 89,780 (1968; C.A. 70 19983q (1969). Wilson discloses 1-hydroxyalkyl-2-imidazolines and specifically, 1-hydroxyethyl--heptadecyl-2-imidazoline, as surface active agents, U.S. Pat. No. 2,267,965 (Dec. 30, 1941) and U.S. Pat. No. 2,268,273 (Dec. 30, 1941). Tryon reported the preparation of compounds 33, 38 and two higher homologs in very low yield, U.S. Pat. No. 2,520,102 (Aug. 22, 1950).

To my knowledge the other compounds are novel.

The use of the compounds of the present invention as penetration enhancers is, however, novel and not predictable from the prior art.

The compounds covered by the general formula I may be prepared by any of the processes known for the preparation of 2-oxazoline derivatives, for example:

(1) Heating a nitrile of formula R—CN with an aminoalcohol of the following formula II in presence of cadmium acetate dihydrate or zinc acetate dihydrate at 100–130°C. with or without a solvent affords the compounds of this invention:

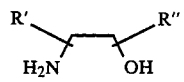

II (wherein R,R' and R" are as defined above) [Witte and Seeliger, Angew. Chem., Int. Ed. Eng., 11, 287-8 (1972); Liebigs Ann. Chem 996-1009 (1974)]. Alternately, an allenic or acetylenic nitrile with an aminoalcohol of formula II on heating gives the compounds of this invention [Fomum et al., Tet. Lett. 1101-4(1975)].

(2) A carboxylic acid, R-COOH, is made to react with an aminoalcohol of the formula II with or without solvent at a temperature of from 150° to 250°C. with elimination of water [Serota et al., J. Org. Chem. 46, 4147-51 (1981); Hersloef and Gronowitz, Chem Scr. 22,230-5 (1983); Frump, Chem. Rev. 71, 483-505 (1971); Meyers and Mihelich, Angew. Chem., Int. Ed. Eng. 15, 270-281(1976)]. In addition compounds, which possess an exocyclic doubledbond on hydrocarbon group R, for example, compounds 20–22, can be prepared according to Serota et al., J.Org.Chem., 46, 4147-51 (1981) from the reaction of 2-alkyl oxazolines with formaldehyde, followed by dehydration. Alternately, aminoalcohol of the formula II may be reacted with an acrylate ester in presence of a catalyst and a polymerization inhibitor, De Benneville and Luskin, U.S. Pat. No. 2,831,858 (Apr. 22, 1958); C.A. 52, 16379h (1958); U.S. Pat. No. 2,897,192 (July 28, 1959); C.A. 54, 585f (1960); Luskin and De Benneville, Ger. Pat. No. 1,067,437 (Oct. 22, 1959); C.A. 55, 19960a (1961). In case of unsubstituted aminoalcohols, the resulting amidoalcohols can be cyclodehydrated as under 3.

(3) Cyclodehydration of an amidoalcohol of formula III

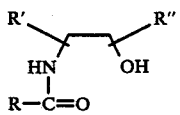

(wherein R, R' and R" are as defined above) to 2-oxazoline derivative is catalyzed by $WO_3 \cdot H_2O$, $NaWO_4 \cdot 2H_2O$, $MoO_2$ and $SrWO_4$ (Litt et al., U.S. Pat. No. 3,681,333 and U.S. Pat. No. 3,681,329, Aug. 1, 1972) or by silica, alumina, silica-alumina or silica-magnesia at 200°–400°C. under reduced pressure [Litt and Levy, U.S. Pat. No. 3,562,263, Feb. 9, 1971; Seeliger and Thier, Justus Liebigs Ann. Chem. 698, 158–66 (1966); Seeliger et al., Angew. Chem., Int. Ed. Eng. 5, 875–88 (1966)]or by treatment with $SOCl_2$, $RSO_2Cl$m $COCl_2$ or $PO(OR)_2Cl$ in order to replace the hydroxyl group by an efficient leaving group that can be eliminated more readily during cyclization [Ishii et al., Yukagaku, 7, 70–4 (1958); C.A. 55, 5993 (1961) and Zioudrou and Schmir, J.Amer.Chem.Soc. 85,3258 (1963)] or simply on heating at high temperature with or without a catalytic amount of a strong mineral acid, De Benneville et al, J. Org. Chem., 23, 1355 (1958).

The amidoalcohol of formula III mentioned above may be prepared from carboxylic acid of formula, R-COOH; from carboxylic acid chloride of formula, R-COCl or from carboxylic acid ester of the formula, R-COOR''' (where R''' is an alkyl group) with an aminoalcohol of formula II mentioned above with or without solvent at a temperature from 0°C. to 150°C. [Wenker, J.Amer.Chem.Soc. 57, 1079 (193 5); D'Alelio an d Emmet Reid, J.Amer.Chem.Soc. 59, 111 (1937); Bassiri et al., Polymer Lett 5, 871–9 (1967)].

(4) Cyclization of the haloamide of the formula IV:

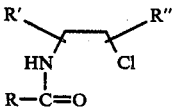

(wherein R, R' and R" are as defined above) with a base such as sodium or potassium hydroxide in aqueous or aqueous alcohol solution or better yet with anhydrous sodium carbonate at an elevated temperature (50° C.-250°C.) under reduced pressure (0.1 mm–30 mm), [Frump, Chem.Rev. 71, 483 (1971) and references cited therein; Bassiri, French Pat. No. 1,477,049, 14 April 1967; Bassiri et al., Polymer Lett. 5, 871–9 (1967);

(5) Addition of an epoxide to a nitrile of the formula, RCN, in concentrated sulfuric acid gives oxazolines of this invention [Oda et al., Bull.Soc.Chem.Japan, 35, 1219 (1962)].

(6) Reaction of an iminoester with an aminoalcohol of formula II mentioned above affords the penetration enhancers of this invention [McCasland and Horswill, J.Amer.Chem.Soc., 73, 3744 (1951); Dornow and Theidel, Chem.Ber. 88, 1267 (1955); and British Pat. No. 704,946 (1954); C.A. 49, 10370 (1956)].

(7) Reaction of an epoxide with an amidine yields oxazolines of this invention [Lambert and Kristofferson, J.Org.Chem., 30, 3938 (1965)].

(8) Treatment of a carboxylic acid of the formula, R-COOH or a carboxylic acid chloride of the formula, RCOCl with ethyleneimine, followed by catalytic isomerization of the carboxylic acid amide gives the oxazolines of this invention [Kagiya et al., Polymer Lett., 4, 441–5 (1966); Heine et al., J.Amer.Chem.Soc., 81 2202 (1959); Fanta and Deutsch, J.Org.Chem , 23,72 (1958); Meyers et al., J.Org.Chem., 39, 2787 (1974); Fukui et al., Japan 69 22,285 (Sept. 24, 1969); C.A. 71, 12449p (1969)].

The heterocyclic compounds containing $X=NR_1$ (wherein $R_1$ is as defined above) covered by the general formula I may be prepared by any one of the classical processes known for the preparation of 2-imidazolines; Ferm and Riebsomer, Chem.Rev. 593 (1954).

For example, treating a diamine of the formula V or its salt (1) with a carboxylic acid of the formula R-COOH, its ester, acid chloride, anhydride, amide, thioamide or nitrile derivative followed by ring closure.

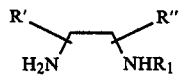

(wherein R, R' and R"$_1$ are as defined above)

The reaction may be carried out in a solvent such as benzene at 130°–230° C. with azeotropic removal of water, Riebsomer, J.Amer.Chem.Soc. 70, 1629 (1948); Harnsberger and Riebsomer, J.Hetro. Chem. 1,188 (1964). The monoacyl or diacyl derivatives formed may or may not be isolated and ring closed, for example, in presence of oxides of calcium or magnesium or other dehydrating agents, Chitwood and Ried, J.Amer.-Chem.Soc. 57, 2424 (1935); Waldman and Chwala, Chem.Ber. 74, 1763 (1941); Fr. Pat. No. 811,423 (Apr.14, 1937); C.A. 31, 8550 (1937); Br. Pat. No. 479,491 (Feb. 7, 1938); C.A. 32, 5002 (1938); U.S. Pat. No. 2,155,877, (Apr. 23, 1939); and 2,155,878 (Apr. 25, 1939); C.A. 33, 5878 (1939), Kyrides and Zienty, U.S. Pat. No. 2,404,300 (July 16, 1946); C.A. 40,6101 (1946); Kyrides, U.S. Pat. No. 2,404,299 (July 16, 1946); C.A. 41,160 (1946); Kyrides and Zienty, U.S. Pat. No. 2,399,601 (Apr. 30, 1946); C.A. 40,4180 (1946); Kyrides, U.S. Pat. No. 2,392,326 (Jan. 8, 1946); C.A. 40,1972 (1946); Aspinall, J.Amer.Chem.Soc. 61,3195 (1939); Hill and Aspinall, J.Amer.Chem.Soc. 61,822 (1939); Kyrides, J.Org.Chem. 12, 577 (1947); Morrill, U.S. Pat. No. 2,508,415 (May 23, 1950); C.A. 45, 668 (1951); Piskov et al., Khim. Geterotsikl. Soedin, 1112 (1976); C.A. 86, 5372h (1977). The nitrile derivative, R-CN, may be reacted with p-toluene sulfonate salt of diamine of formula V, Oxley and Short, J.Chem.Soc. 497 (1947), Savignac et al., J.Hetero.Chem. 15, 897 (1978) or with diamine of formula V in presence of catalytic amount of sulfur, Sawa, Nippon Kagaku Zasshi, 89, 780 (1968); C.A. 70, 19983q (1969) or in presence of catalytic amount of carbon disulfide at 80°–190° C. for 1 to 48 hours, Hueni, U.S. Pat. No. 2,868,802 (Jan. 13, 1959); Fruhstorfer and Muller-Calagan, Ger. Pat. No.

1,117,588 (Nov. 23, 1961); Hansen, Ger. Pat. No. 1,670,143 (May 30, 1974);

(2) with the imidates of the formula

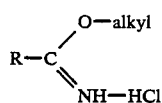

or amidines of the formula

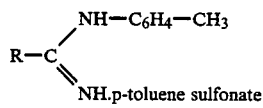

Bockmuhl and Knoll, U.S. Pat. No. 1,958,529 (May 15, 1934); C.A. 28,4539 (1934); Oxley and Short, J.Chem.-Soc. 497 (1947); Short and Oxley, Brit. Pat., 614,032 (Dec. 8, 1948); C.A. 43,5049 (1949); I. G. Farbenindustrie A.G., Fr. Pat. 671,362 (Mar. 12, 1929).

The imidazolines may be prepared by treating the imidates mentioned above with aminoalcohol of formula II, Drozdov and Bekhli, J.Gen.Chem U.S.S.R. 14,480 (1944); C.A. 39,4590 (1945) or by heating a mixture of a carboxylic acid of the formula R-COOH and a 2-imidazolidone at 250°–300°C., I. G. Farbenindustrie A.G., Brit. Pat. No. 492,812 (Sept. 28, 1938); C.A. 33,1761 (1939).

Finally, 2-imidazolines may be prepared by reducing monoacyl derivatives of alpha aminonitriles in presence of a reducing agent, for example, Raney nickel, Hawkins and Biggs, J.Amer.Chem.Soc. 71,2530 (1949); Hawkins, U.S. Pat. No. 2,587,043 (Feb. 26, 1952); C.A. 46,9122 (1952).

N-substituted 2-imidazolines my be prepared by alkylation of 2-substituted 2-imidazolines with an alkyl halide in presence of a strong base such as sodium hydride in hexamethylphosphotriamide (HMPT) or an organolithium compound, for example, butyl lithium in an inert solvent according to Cognacq, British Pat. No. 1,417,174 (Dec. 10, 1975).

The compounds of the present invention may be used as penetration enhancers in the same manner as described in my U.S. Pat. Nos. 3,989,816; 3,991,203; 4,415,563; 4,122,170; 4,316,893; 4,423,040; 4,424,210; 4,444,762 and pending U.S. Application Ser. No. 783,621 filed Sept. 30, 1985, which are hereby incorporated by reference.

The compounds of the present invention are useful as penetration enhancers for a wide range of physiologically active agents and the compositions disclosed herein are useful for topical and transdermal therapeutic effect of these agents. Typically systemically active agents which may be delivered transdermally are therapeutic agents which are sufficiently potent such that they can be delivered through the skin or other membranes to the bloodstream in sufficient quantities to produce the desired therapeutic effect. In general this includes agents in all of the major therapeutic areas including, but not limited to, anti-infectives, such as antibiotics and antiviral agents, analgesics, anorexics, anthelmintics, antiarthritics, antiasthma agents, anticonvulsants, antidepressants, antidiabetic agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarryhthmics, antihypertensives, diuretics, vasodilators including general, coronary, peripheral and cerebral; central nervous system stimulants, cough and cold preparations, decongestants, diagnostics, hormones, hypnotics, immunosuppressives, muscle relaxants, parasympatholytics, parasympathomimetics, sedatives, tranquilizers and anti-osteoporosis agents.

For topical applications the agents include antibiotics, fungistatic and fungicidal agents, corticosteroids, anti-inflammatory agents, antiemetics, antipruritic agents, vasodilators, bronchodilators, expectorants, analgesics, anti-osteoporosis agents, sunscreen compounds, collagen softening agents and other similar compounds. Cosmetic agents, hair and skin dyes, natural and synthetic hormones, perfumes, insect repellents, diagnostic agents and other such compounds may also be advantageously formulated with these penetration enhancers.

Moreover, these penetration enhancers are useful in agriculture in the application of fertilizers, hormones, growth factors including micronutrients, insecticides, molluscicides, arachides, nematocides, rodenticides, herbicides, and other pesticides to plants, animals and pests. These penetration enhancers are also useful for penetration of micronutrients and chemical hybridization agents in seeds for enhanced plant growth.

Of course, the appropriate dosage levels of all the physiologically active agents, without conjoint use of the penetration enhancing compounds of formula I, are known to those of ordinary skill in the art. These conventional dosage levels correspond to the upper range of dosage levels for compositions including a physiologically active agent and a compound of formula I as a penetration enhancer. However, because the delivery of the active agent is enhanced by compounds of the present invention, dosage levels significantly lower than conventional dosage levels may be used with success. Systemically active agents are used in amounts calculated to achieve and maintain therapeutic blood levels in a human or other animal over the period of time desired. (The term "Animal" as used here encompasses humans as well as other animals, including particularly pets and other domestic animals ) These amounts vary with the potency of each systemically active substance, the amount required for the desired therapeutic or other effect, the rate of elimination or breakdown of the substance by the body once it has entered the bloodstream and the amount of penetration enhancer in the formulation. In accordance with conventional prudent formulating practices, a dosage near the lower end of the useful range of a particular agent is usually employed initially and the dosage increased or decreased as indicated from the observed response, as in the routine procedure of the physician.

The present invention contemplates compositions of compounds of formula I, together with physiologically active agents from 0.05% to 100% of conventional dosage levels. The amount of oxazoline or imidazoline which may be used in the present invention is an effective, non-toxic amount for enhancing percutaneous absorption. Generally, for topical use the amount ranges between 0.01 to about 10 and preferably about 0.1 to 5 percent by weight of the composition. For transdermal enhancement of systemic agents, the amount of penetration enhancer which may be used in the invention varies from about 1 to 100 percent although adequate enhancement of penetration is generally found to occur in the range of about 1 to 30 percent by weight of the formulation to be delivered. For transdermal use, the penetration enhancers disclosed herein may be used in combination with the active agent or may be used separately as a pre-treatment of the skin or other body membranes through which the active agent is intended to be delivered.

Dosage forms for application to the skin or other membranes of humans and animals include creams, lotions, gels, ointments, suppositories, sprays, aerosols, buccal and sublingual tablets and any one of a variety of transdermal devices for use in the continuous administration of systemically active drugs by absorption through the skin, oral mucosa or other membranes, see for example, one or more of U.S. Pat. Nos. 3,598,122; 3,598,123; 3,731,683; 3,742,951; 3,814,097; 3,921,636; 3,972,995; 3,993,072; 3,992,073; 3,996,934; 4,031,894; 4,060,084; 4,069,307; r,201,211; 4,230,105; 4,292,299 and 4,292,303. U.S. Pat. No. 4,077,407 and the foregoing patents also disclose a variety of specific systemically active agents which may also be useful as in transdermal delivery, which disclosures are hereby incorporated herein by this reference.

The penetration enhancers of this invention may also be used in admixture with other penetration enhancers disclosed earlier and incorporated herein by reference.

Typical inert carriers which may be included in the foregoing dosage forms include conventional formulating materials, such as, for example, water, ethanol, 2-propanol, 1,2-propanediol, 1,3-butanediol, 1,2,3,-propanetriol, propanone, butanone, carboxylic acid esters such as isopropyl myristate, diisopropyl adipate and diisopropyl sebacate, acyclic and cyclic amides including N-methyl pyrrolidone, freons, PEG-200, PEG-400, Polyvinyl pyrrolidone, fragrances, gel producing materials such as "Carbopol", stearyl alcohol, stearic acid, spermaceti, sorbitan monooleate, sorbital, "polysorbates", "Tweens", methyl cellulose etc.

It will be readily appreciated by those skilled in the art that certain compounds represented by formula I exhibit chirality. However, where no designation of isomers is specified with respect to the compounds of this invention, it is to be understood that all possible stereoisomers are included.

The examples which follow illustrate the penetration enhancers and the compositions of the present invention. However, it is understood that the examples are intended only as illustrative and are not to be construed as in any way limiting to scope of this invention.

EXAMPLE 1

Preparation of 2-undecyl-2-oxazoline

The reaction was carried out under nitrogen atmosphere in a three neck flask equipped with a magnetic stirring bar, reflux condenser, addition funnel and thermometer. 50 ml of 1-butanol and 667 mg (2.5 mmoles) of cadmium acetate dihydrate was introduced and the catalyst was dissolved by slight warming. 18.13 g (100 mmoles) of undecyl cyanide was added and the solution was heated to 125° C. 7.33 g (120 mmoles) of 2-aminoethanol was then added dropwise controlling the evolution of ammonia. At the end of the reaction (ca. 48 hrs.) the solvent was removed under vacuo. The residue was treated with 100 ml of petroleum ether and filtered after keeping for several hours. The filtrate was washed with water, dried over anhydrous magnesium sulfate, concentrated and the residue was distilled 114° C./0.5mm to give 19.83 g (88%) of 2-undecyl-2oxazoline.

EXAMPLE 2

Preparation of 2-decyl-2-oxazoline

Undecyl cyanide in Example 1 was substituted with 18.13 g (108.4 mmoles) of undecanenitrile and allowed to react with 7.5 ml (121.3) mmoles of aminoethanol in presence of cadmium acetate dihydrate (667 mg; 2.5 mmoles) in 1-butanol under identical reaction conditions. The reaction mixture was worked up following Example 1 and the residue was distilled at 118°–120°/1.2 mm to give 14.72 g (64.3%) of 2-decyl-2oxazoline.

EXAMPLE 3

Preparation of 2-heptadecyl-2-oxazoline

Undecyl cyanide in Example 1 was substituted with 26.55 g (100 mmoles) of heptadecyl cyanide and the reaction was repeated under identical conditions. The residue, after removal of 1-butanol under vacuo, was extracted with 150 ml of toluene at 70° C. and filtered. The filtrate was washed with water, dried, concentrated and the residue on slight wash with acetonitrile gave 23.79 g (77%) of 2-heptadecyl-2-oxazoline, m.p. 52°–53°C.

EXAMPLE 4

Preparation of 2-pentyl-2-oxazoline 9.72 g (100 mmoles) of hexanenitrile was substituted for undecyl cyanide in Example 1 and the reaction was repeated with 6.11 g (100 mmoles) of ethanolamine and 549 mg (2.5 mmoles) of zinc acetate dihydrate under identical conditions. At the end of the reaction the product was worked up as before and distilled at 73° C./10 mm to give 8.2 g (60%) of 2-pentyl-2-oxazoline.

EXAMPLE 5

The following compounds are prepared analogously following Example 1 and substituting the undecyl cyanide by the appropriate alkyl cyanide and reacting it with aminoethanol in same molar ratio.

2-heptyl-2-oxazoline
2-nonyl-2-oxazoline
2-tridecyl-2-oxazoline
2-pentadecyl-2-oxazoline

EXAMPLE 6

Preparation of 4-methyl-2-undecyl-2-oxazoline 10.9 g (60 mmoles) of undecyl cyanide was treated with 5 g (66.6 mmoles) of DL-2-amino-1-propanol in presence of 400 mg (1.5 mmoles) of cadmium acetate dihydrate in 1-butanol as outlined under Example 1. 13.2 g (92%) of product was obtained on distillation at 115°–117° C./1–1.5 mm Hg.

EXAMPLE 7

The following compounds are prepared analogously following Example 6 and substituting undecyl cyanide by 60 mmoles of the appropriate alkyl cyanide.

4-methyl-2-heptyl-2-oxazoline
4-methyl-2-nonyl-2-oxazoline
4-methyl-2-undecyl-2-oxazoline
4-methyl-2-tridecyl-2-oxazoline
4-methyl-2-pentadecyl-2-oxazoline
4-methyl-2-heptadecyl-2-oxazoline

EXAMPLE 8

The following compounds are prepared analogously following Example 6 and substituting DL-2-amino-1-propanol by 66.6 mmoles of the appropriate aminoalcohol.
4-Trifluoromethyl-2-undecyl-2-oxazoline
4-Isopropyl-2-undecyl-2-oxazoline
4-t-Butyl-2-undecyl-2-oxazoline

EXAMPLE 9

Preparation of 4-ethyl-2-undecyl-2-oxazoline 25 g (137.9 mmoles) of undecyl cyanide was treated with 15.2 ml (165 mmoles) of DL-2-amino-1-butanol in presence of 919 mg (3.54 mmoles) of cadmium acetate dihydrate in 1-butanol as outlined under Example 1. 31.31g (89.6%) of product was obtained on distillation at 124°–125°C./1.2–1.4mmHg.

EXAMPLE 10

The following compounds are prepared analogously following Example 10 and substituting undecyl cyanide by 137.9 mmoles of the appropriate alkyl cyanide.
4-ethyl-2-pentyl-2-oxazoline
4-ethyl-2-heptyl-2-oxazoline
4-ethyl-2-nonyl-2-oxazoline
4-ethyl-2-decyl-2-oxazoline
4-ethyl-2-tridecyl-2-oxazoline
4-ethyl-2-pentadecyl-2-oxazoline
4-ethyl-2-heptadecyl-2-oxazoline

EXAMPLE 11

Preparation of 4,4-dimethyl-2-undecyl-2-oxazoline 64 g (320 mmoles) of dodecanoic acid and 61.1 ml (640 mmoles) of 2-amino-2-methylpropanol was placed in a two neck flask equipped with a vigreux column, distillation condenser and a thermometer. The temperature of the reaction mixture was slowly brought to 180° C. and maintained there for 9 hours. After cooling, a 10% alcoholic KOH solution (2 g, 3.6 mmoles) was added and the reflux was continued at 180° C. for 4 hours. The excess 2-amino-2-methylpropanol was distilled at aspirator pressure (86°C./ 18 mm). When the vapor temperature reached 103° C., the distillation was discontinued and the residue was taken in petroleum ether and filtered. The filtrate was washed with dilute KOH, water, dried and concentrated. The oil was distilled at 120° C./ 1.2 mmHg to give 70.5 g (87%) of product.

EXAMPLE 12

Preparation of 4,4-dimethyl-2-pentyl-2-oxazoline

Following the procedure under Example 11, 6.085 g (52.4 mmoles) of hexanoic acid and 10 ml (9.34 g, 104.8 mmoles) of 2-amino-2-methylpropanol was heated to 185°C. Work up and fractional distillation gave 7.2g (81%) of product, b.p. 90°–92° C./25mmHg.

EXAMPLE 13

Preparation of 4,4-dimethyl-2-heptadecyl-2-oxazoline

Following example 11, 14.9 g (52.4 mmoles) of octadecanoic acid and 9.34 g (104.8 mmoles) of 2-amino-2-methylpropanol gave 14.1 g (79.7%) of product, b.p. 140°–143° C./0.01 mmHg.

EXAMPLE 14

The following compounds are prepared analogously following the procedure under Example 11 and substituting the dodecanoic acid by the appropriate alkanoic acid.
4,4-dimethyl-2-heptyl-2-oxazoline
4,4-dimethyl-2-nonyl-2-oxazoline
4,4-dimethyl-2-tridecyl-2-oxazoline
4,4-dimethyl-2-pentadecyl-2-oxazoline

EXAMPLE 15

Preparation of 4,4-Dimethyl-2-(1-dodecen-2-yl)-2-oxazoline 4.2 g (141 mmoles) of paraformaldehyde was added to 22.5 g (88.8 mmoles) of 4,4-dimethyl-2-undecyl-2oxazoline (obtained in Example 11) at 90° C. The mixture was stirred at 90° C. for 30 minutes and the temperature was raised by 5° C. increment every half hour up to 115° C. 20 ml of cumene was added and the mixture was refluxed for 2.5 hours at 180° C. with removal of water using a Dean-Stark trap. The solution was distilled at 126°–129°C./1mm to give 18.2 g of product. This contained 5–10% starting oxazoline. LPLC purification on 40–60 micron silica gel (petroleum ether to 90% petroleum ether/ethyl acetate gradient) gave 16.5 g (70%) of pure product.

EXAMPLE 16

The following compounds are prepared analogously following Example 15 and substituting the 4,4-dimethyl-2-undecyl-2-oxazoline by equimolar amounts of the corresponding 4-trifluoromethyl and 4-methyl-4trifluoromethyl derivatives.
4-Trifluoromethyl-2-(1-dodecen-2-yl)-2-oxazoline
4-Methyl-4-trifluoromethyl-2-(1-dodecen-2-yl-2oxazoline

EXAMPLE 17

Preparation of 4-hydroxymethyl-4-methyl-2-undecyl-2-oxazoline

A mixture of 20.03 g (100 mmoles) of dodecanoic acid and 11.57 g (110 mmoles) of 2-amino-2-methyl-1,3propanediol in 10 ml of xylene was heated for 30 hours at 185°–190°C. with azeotropic removal of water. The reaction mixture was taken up in ethyl acetate and was washed with water to remove excess amino alcohol. The organic layer was dried, concentrated and the residue was distilled at 152°–155° C./ 1 mmHg to give 22.8 g (84.6%) of 4-hydroxymethyl-4-methyl-2-undecyl-2oxazoline.

EXAMPLE 18

The following compounds are prepared analogously following Example 17 and substituting the dodecanoic acid by equimolar amount of the appropriate alkanoic acid.
4-hydroxymethyl-4-methyl-2-nonyl-2-oxazoline
4-hydroxymethyl-4-methyl-2-tridecyl-2-oxazoline
4-hydroxymethyl-4-methyl-2-pentadecyl-2-oxazoline
4 hydroxymethyl-4-methyl-2-heptadecyl-2-oxazoline

EXAMPLE 19

Preparation of 4-hydroxymethyl-4-ethyl-2-undecyl-2-oxazoline 26 g (130 mmoles) of dodecanoic acid and 31 g (260 mmoles) of 2-amino-2-ethyl-1,3-propanediol were condensed together by heating at 185°–190° C. for 30 hours. Work up and distillation of the residue at 160°–162° C./1 mm Hg gave 33.19 g (90%) of the product.

EXAMPLE 20

The following compounds are prepared analogously following Example 19 and substituting the dodecanoic acid by equimolar amount of an appropriate alkanoic acid.
4-hydroxymethyl-4-ethyl-2-octyl-2-oxazoline
4-hydroxymethyl-4-ethyl-2-nonyl-2-oxazoline
4-hydroxymethyl-4-ethyl-2-tridecyl-2-oxazoline
4-hydroxymethyl-4-ethyl-2-pentadecyl-2-oxazoline
4-hydroxymethyl-4-ethyl-2-heptadecyl-2-oxazoline

EXAMPLE 21

Preparation of 2-(2-dodecyl)-2-oxazoline 100 mmoles of 2-cyanododecane is treated with 120 mmoles of 2-aminoethanol in 50 ml of 1-butanol in presence of 2.5 mmoles of cadmium acetate dihydrate as outlined under Example 1 to give 2-(2-dodecyl)-2oxazoline.

EXAMPLE 22

The following compounds are prepared analogously following Example 21 and substituting 2-aminoethanol by 120 mmoles of the appropriate 2-aminoalkanol derivative.
4-Methyl-2-(2-dodecyl)-2-oxazoline
4-Isopropyl-2-(2-dodecyl)-2-oxazoline
4-t-Butyl-2-(2-dodecyl)-2-oxazoline
4-Trifluoromethyl-2-(2-dodecyl)-2-oxazoline

EXAMPLE 23

Preparation of 2-(2-Methyl-2-decyl)-2-oxazoline 100 mmoles of 2-cyano-2-methyldodecane is reacted with 120 mmoles of 2-aminoethanol in 50 ml of 1-butanol in presence of 2.5 mmoles of cadmium acetate dihydrate as outlined under Example 1 to give 2-(2-methyl-2-decyl)-2-oxazoline.

EXAMPLE 24

The following compounds are prepared analogously following Example 23 and substituting 2-aminoethanol by 120 mmoles of the appropriate 2-aminoalkanol derivative.
4-Methyl-2-(2-methyl-2-decyl)-2-oxazoline
4-Isopropyl-2-(2-methyl-2-decyl)-2-oxazoline
4-Trifluormethyl-2-(2-methyl-2-decyl)-2-oxazoline

EXAMPLE 25

Preparation of 4,4-Dimethyl-2-(2-dodecyl)-2-oxazoline 10 g of 4,4-Dimethyl-2-(1-dodecen-2-yl)-2oxazoline, obtained in Example 15, was dissolved in 200 ml ethanol and hydrogenated in a Parr apparatus over 1 g of 10% Pd/C at 50 p.s.i. The catalyst was removed and the filtrate was concentrated to give the product. This was distilled at 120°–122°/0.8 mm to give 9.68 g (96.5%) of colorless product.

EXAMPLE 26

Preparation of 4,4-Dimethyl-2-(2-methyl-3-tridecyl)-2-oxazoline

A solution of 25.34 g (100 mmoles) of 4,4-dimethyl-2-undecyl-2-oxazoline in 250 ml of dry THF under nitrogen atmosphere was cooled to −78° C. To this was added 62.5 ml (100 mmoles) of 1.6M solution of n-butyl lithium in hexane over a period of 15 minutes and the solution was further stirred for 2 hours. 18.45 g (150 mmoles) of 2-bromopropane was added at −78° C. over a period of 30 minutes and the resulting solution was allowed to warm to room temperature overnight. The solution was poured into 250 ml of saturated ammonium chloride solution and the organic phase was separated. The aqueous phase was extracted with 2×100 ml of ether, the organic phases were combined and extracted with 2×200 ml of brine. After drying over anhydrous magnesium sulphate, the solution was concentrated and the residue was distilled at reduced pressure 10.2 g of starting material was recovered. 8.82 g (50% based on recovered starting material) of product distilled at 131°–134° C./ 0.8 mm Hg. 2.98 g (14.8%) of disubstituted product was obtained as a higher boiling fraction.

EXAMPLE 27

Preparation of 2-Undecyl-2-imidazoline 18.32g (100 mmoles) of undecyl cyanide, 8.5ml (127 mmole) of ethylenediamine and 0.5ml of carbon disulfide were mixed and heated in an oil bath at 125° C. for 24 hours. The reaction mixture was cooled, treated with dilute hydrochloric acid and treated with charcoal. The light yellow filtrate was extracted with ethyl acetate, the organic extracts dried over magnesium sulfate and concentrated. The residue was Kugelrohr distilled and then recrystallized from toluene. Yield 13.7 g (61.1), m.p. 82° C.

EXAMPLE 28

The following compounds were prepared analogously following Example 27 and substituting the undecyl cyanide by equimolar amount of the appropriate alkyl cyanide.
2-Pentyl-2-imidazoline
2-Heptyl-2-imidazoline
2-Nonyl-2-imidazoline
2-Tridecyl-2-imidazoline
2-Pentadecyl-2-imidazoline

EXAMPLE 29

Preparation of 1-Methyl-2-heptyl-2-imidazoline 14.207 g (113.46 mmoles) of heptyl cyanide, 10.726 g (144.69 mmoles) of N-methylethylenediamine and 0.5 ml of carbon disulfide were mixed and heated at 125° C. for 24 hours. The solution was cooled, diluted with ethyl acetate and extracted with dilute hydrochloric acid. The acidic solution was basified with sodium hydroxide and extracted with ethyl acetate. The organic extracts were treated with charcoal, filtered, concentrated and Kugelrohr distilled at 105° C./1 2mm to give 19.73 g (77.3%) of the product.

EXAMPLE 30

Preparation of 1-Hydroxyethyl-2-octyl-2-imidazoline 13.02 g(93.51 mmoles) of octyl cyanide was treated with 12.327 g (118.36 mmoles) of 2-(2-amino ethylamino)ethanol in presence of 0.5ml of carbon disulfide at 125° C. for 24 hrs. and worked up as outlined under Example 29. Distillation of the residue at 167°-169°/0.5mm gave 12.332g (62.7%) of product.

EXAMPLE 31

Preparation of 1-Isopropyl-2-undecyl-2-imidazoline
18.324 g of Undecyl cyanide, 15.12 g of N-isopropylethylene-diamine and 0.5 ml of carbon disulfide were heated at 125° C. for 24 hrs. and worked up as mentioned under Example 29, followed by distillation at 150°C./1.2mm gave 21.93 g (82.3%) of the product.

EXAMPLE 32

The following compounds are prepared analogously following Example 31 and substituting the undecyl cyanide by equimolar amount of the appropriate alkyl cyanide.
1-Isopropyl-2-pentyl-2-imidazoline
1-Isopropyl-2-heptyl-2-imidazoline
1-Isopropyl-2-nonyl-2-imidazoline
1-Isopropyl-2-tridecyl-2-imidazoline
1-Isopropyl-2-pentadecyl-2-imidazoline

EXAMPLE 33

Preparation of 4-Methyl-2-undecyl-2-imidazoline 18.31 g (100 mmoles) of undecyl cyanide, 9.3 g (125 mmoles) of 1,2-diaminopropane and 0.5 ml of carbon disulfide were heated to 125°C. for 24 hrs. and then worked up as mentioned under Example 29. Kugelrohr distillation at 163°-165° C./1.2-1.4mm Hg gave 17.85 g (75%) of product.

EXAMPLE 34

The following compounds are prepared analogously following Example 33 and substituting the 1,2 -diaminopropane by equimolar amount of the appropriately substituted 1,2-diamine.
4-Isopropyl-2-undecyl-2-imidazoline
4-t-Butyl-2-undecyl-2-imidazoline
4-trifluoromethyl-2-undecyl-2-imidazoline

EXAMPLE 35

Preparation of 4,4-Dimethyl-2-undecyl-2-imidazoline
18.31 g (100 mmoles) of undecl cyanide, 11 g (125 mmoles) of 1,2-diamino-2-methylpropane and 0.5 ml of carbon disulfide were heated at 125° C. for 24 hrs. and then worked up as under Example 29. Distillation at reduced pressure gave 19.66 g (78%) of the product.

EXAMPLE 36

The following compounds are prepared analogously following Example 35 and substituting the undecyl cyanide by equimolar amount of the appropriate alkyl cyanide
4,4-Dimethyl-2-pentyl-2-imidazoline
4,4-Dimethyl-2-heptyl-2-imidazoline
4,4-Dimethyl-2-nonyl-2-imidazoline
4,4-Dimethyl-2-tridecyl-2-imidazoline

EXAMPLE 37

Preparation of 4-Methyl-4-t-butyl-2-undecyl-2-imidazoline
15 g of 2-cyano-2-decanoylamino-3,3-dimethylbutane (prepared from acylation of aminonitrile obtained from treatment of pinacolone with sodium cyanide and ammonium chloride) in 250 ml of 95% ethanol and 70 ml of ammonium hydroxide was hydrogenated with T-1 Raney Nickel. The catalyst was filtered off. The filtrate was concentrated and the residue was distilled at reduced pressure to give 7.5 g (52%) of the product.

EXAMPLE 38

The following compounds are prepared analogously following Example 37 and substituting the 2-cyano-2-dodecanoylamino-3,3-dimethylbutane by equimolar amount of the appropriate 2-cyano-2-acylaminoalkane.
4-Methyl-4-isopropyl-2-undecyl-2-imidazoline
4,4-Diisopropyl-2-undecyl-2-imidazoline
4-Methyl-4-trifluoromethyl-2-undecyl-2-imidazoline

EXAMPLE 39

Preparation of 4,4-Dimethyl-1-isopropyl-2-undecyl-2-imidazoline
22.84 g. (100 mmoles) of ethyl laurate and 15.34 g. (118 mmoles) of $N^l$-isopropyl-2-methyl-1,2-propanediamine is heated at 130°-230° C. until approximately 100 mmoles of ethanol is collected. Toluene is then cautiously added and the heating is continued until no more water separates. The solution is acidified, the aqueous layer is separated and basified with NaOH. This is extracted with ethyl acetate, the organic extract is dried and concentrated. The oil is distilled at 150–152° C./1.2 mm to give 16.74 g (58%) of product.

EXAMPLE 40

The following compounds are prepared analogously following Example 39 and substituting the ethyl laurate by equimolar amount of the appropriate carboxylic acid lower alkyl ester.
4,4-Dimethyl-1-isopropyl-2-pentyl-2-imidazoline
4,4-Dimethyl-1-isopropyl-2-heptyl-2-imidazoline
4,4-Dimethyl-1-isopropyl-2-nonyl-2-imidazoline
4,4-Dimethyl-1-isopropyl-2-tridecyl-2-imidazoline
4,4-Dimethyl-1-isopropyl-2-pentadecyl-2-imidazoline
4,4-Dimethyl-1-isopropyl-2-heptadecyl-2-imidazoline

EXAMPLE 41

Preparation of 4,4-Dimethyl-1-n-butyl-2-undecyl-2imidazoline 22 ml (55 mmoles) of a 2.5M solution of butyl lithium in hexane are added to 12.62g (50 mmoles) of 4,4-dimethyl-2-undecyl-2-imidazoline in 50 ml of anhydrous benzene at a temperature kept at around 20° C. The mixture is then stirred for 2 hours at ambient temperature (15° to 20° C.). 8.22 g (60 mmoles) of 1 -bromobutane is then added dropwise to the reaction mixture, keeping the temperature at around 20° C. The reaction mixture is then stirred at ambient temperature until it is homogeneous, after which it is refluxed for 3 hours. After cooling, 50 ml of water is added, the mixture is stirred for half hour, decanted and extracted with 100 ml of ether. After drying over magnesium sulfate the solvent is removed in vacuo and the oil is distilled at reduced pressure to give 10.34 g (67%) of the product.

EXAMPLE 42

The following compounds are prepared analogously following Example 41 and substituting 1-bromobutane by an equimolar amount of the appropriate alkyl halide.
1,4,4-Trimethyl-2-undecyl-2-imidazoline
4,4-Dimethyl-1-ethyl-2-undecyl-2-imidazoline
4,4-Dimethyl-1-n-propyl-2-undecyl-2-imidazoline
4,4-Dimethyl-1-isopropyl-2-undecyl-2-imidazoline 4,4-Dimethyll-s-butyl-2-undecyl-2-imidazoline

EXAMPLE 43

Preparation of 2-(2-Dodecyl)-2-imidazoline 19.53 g (100 mmoles) of 2-cyanododecane, 8.5ml (127 mmoles) of ethylenediamine and 0.5 ml of carbon disulfide are reacted according to Example 29 and the reaction mixture is worked up as mentioned therein. Distillation of the residue gives 15.5 g (65%) of the product.

EXAMPLE 44

The following compounds are prepared analogously following Example 43 and substituting the ethylenediamine with an equimolar amount of alkylenediamine:

1-Hydroxyethyl-2-(2-dodecyl)-2-imidazoline
1-Methyl-2-(2-dodecyl)-2-imidazoline
1-Isopropyl-2-(2-dodecyl)-2-imidazoline
4,4-Dimethyl-2-(2-dodecyl)-2-imidazoline
4,4-Dimethyl-1-isopropyl-2-(2-dodecyl)-2imidazoline.

EXAMPLE 45

Preparation of 2-(2-Methyl-2-decyl)-2-imidazoline 18.32 g (100 mmoles) of 2-cyano-2-methyldecane, 8.5 ml (127 mmoles) of ethylenediamine and 0.5 ml of carbon disulfide are reacted according to Example 29 and the reaction mixture is worked up as mentioned therein. Distillation of the residue gives 13.91 g (62%) of the product.

EXAMPLE 46

The following compounds are prepared analogously following Example 45 and substituting the ethylenediamine with an equimolar amount of alkylenediamine.
1-Hydroxyethyl-2-(2-methyl-2-decyl)-2-imidazoline
1-Methyl-2-(2-methyl-2-decyl)-2-imidazoline
1-Isopropyl-2-(2-methyl-2-decyl)-2-imidazoline
4,4-Dimethyl-2-(2-methyl-2-decyl)-2-imidazoline
4,4-Dimethyl-1-isopropyl-2-(2-methyl-2-decyl)-2-imidazoline

EXAMPLE 47

The compounds of Examples 11, 17, 27, 31 and 37 were tested as penetration enhancing agents according to the procedure below:

Skin from female hairless mice, 8–12 weeks old, was removed from the animals and placed between the donor and the receptor compartments of diffusion cells, with normal saline (pH 7.2–7.4) bathing corium. The skin was incubated at 37° C. and the ambient humidity.

100 microliters of the solution containing 1 mg of test drug was applied to the epidermal surface within the donor compartment. The entire contents from the 4.2 ml receptor compartment bathing the corium were removed for analysis at 5 or 6, 12 and 24 hours intervals. In each case, the receptor compartment was refilled with 4.2 ml of fresh normal saline.

The aliquots removed after 5 or 6, 12 and 24 hours were analyzed by HPLC using a C-18 reverse phase column. The test solutions used in this experiment contained 1% Hydrocortisone, 2% 1,2-propanediol and 2% penetration enhancer. The control solution did not have penetration enhancer. 1-Dodecylhexahydro-2H-azepin-2-one, Azone (Registered Trademark), described in the U.S. Patents of this inventor as having good penetration enhancing properties, was used for comparison. Another penetration enhancer, 1-Dodecanoylhexahydro-1H-azepine, disclosed in my related U.S. application Ser. No. 783,621, filed on Sept. 30, 1985, was also included for comparison.

The results, as reported in Table 1 below, are average for two cells and clearly show that the compounds of Examples 11, 27, 31 and 37 have far superior penetration enhancing properties as compared to the control, 1-Dodecylhexahydro-2H-azepine-2-one (Azone) and 1-Dodecanoylhexahydro-1H-azepine. The latter two, as evident from this experiment, are equivalent as to their enhancing property.

TABLE 1

| Penetration Enhancer | % Penetration hrs. | | | |
|---|---|---|---|---|
| | 5 | 6 | 12 | 24 |
| (1) 1-Dodecanoylhexahydro-1-H-azepine | — | 16.2 | 23.0 | 34.9 |
| (2) Example 11 | — | 16.1 | 28.2 | 49.1 |
| (3) Example 17 | — | 8.8 | 17.3 | 34.9 |
| (4) 1-Dodecylhexahydro-2H-azepine-2-one, Azone(TM) | — | 16.9 | 22.6 | 34.4 |
| (5) -same as above- | 7.8 | — | 17.0 | 32.8 |
| (6) Example 27 | 34.8 | — | 42.1 | 43.7 |
| (7) Example 31 | 44.9 | — | 53.0 | 54.2 |
| (8) Example 37 | 35.0 | — | 47.8 | 51.8 |
| (9) Control | — | 1.3 | 1.8 | 2.4 |

EXAMPLE 48

The compounds of Examples 11 and 31 were tested as penetration enhancers according to the procedure outlined under Example 47. 1% hydrocortisone in the formulations of Example 47 was substituted by 1% 5-fluorouracil. 1-Dodecylhexahydro-2H-azepin-2-one (Azone - Trademark), was used for comparison. The results are outlined in Table 2 and clearly show that the compound of Example 11 is comparable and the compound of Example is superior to 1-dodecylhexahydro-2H-azepin-2-one.

TABLE 2

| | Penetration enhancer | % Penetration hrs | | |
|---|---|---|---|---|
| | | 6 | 12 | 24 |
| (1) | Dodecylhexahydro-2H-azepin-2-one | 58.4 | 62.9 | 64.1 |
| (2) | Example 11 | 59.2 | 60.3 | 60.5 |
| (3) | Example 31 | 74.7 | 80.2 | 80.7 |
| (4) | Control | 8.7 | 10.4 | 10.9 |

EXAMPLE 49

The following formulation is prepared.

| | Solution % |
|---|---|
| Griseofulvin | 1 |
| 1-Isopropyl-2-undecyl-2-imidazoline | 1 |
| $C_{12}$-$C_{15}$ benzoate | 5 |
| Fragrance | 0.1 |
| Ethanol | 92.9 |

This formulation is effective in the treatment of fungus infection.

EXAMPLE 50

An aerosol form of the formulation of Example 35 is prepared by preparing the following mixture:

| | |
|---|---|
| Formulation | 25% |
| Freon [1] | 75% |

[1] Freon is 75/25 Freon 114/12

EXAMPLE 51

The following cream formulation is prepared:

| | % |
|---|---|
| Clindamycin Base | 1.0 |
| Stearyl alcohol, U.S.P. | 12.0 |
| Ethoxylated cholesterol | 0.4 |
| Synthetic spermaceti | 7.5 |
| Sorbitan monooleate | 1.0 |
| Polysorbate 80, U.S.P. | 3.0 |
| 1-Isopropyl-2undecyl-2-imidazoline | 0.9 |
| Sorbitol solution, U.S.P. | 5.5 |
| Sodium citrate | 0.5 |
| Chemoderm #844 | 0.2 |
| Purified water | 68.0 |

This formulation is effective in the treatment of acne.

EXAMPLE 52

The following solution formulations are prepared:

| | A (%) | B (%) |
|---|---|---|
| Clindamycin base | — | 1.0 |
| Clindamycin phosphate acid | 1.3 | — |
| Sodium hydroxide | 0.077 | — |
| 1 M Hydrochloric acid | — | 2.27 |
| Disodium edentate.2H$_2$O | 0.003 | 0.003 |
| Fragrances | 0.5 | 0.5 |
| 1-Isopropyl-2-undecyl-2-imidazoline | 1.0 | 1.0 |
| Purified water | 20.0 | 17.73 |
| Isopropanol | 77.12 | 77.497 |

These solutions are effective for the treatment of acne in humans.

EXAMPLE 53

The following solution formulation is prepared:

| | % |
|---|---|
| Neomycin sulfate | 0.5 |
| Lidocaine | 0.5 |
| Hydrocortisone | 0.25 |
| 1-Isopropyl-2-undecyl-2-imidazoline | 1.0 |
| Propylene glycol | 97.75 |

This solution is effective for the treatment of otitis in domestic animals.

EXAMPLE 54

The following sunscreen emulsion is prepared:

| | % |
|---|---|
| PABA | 2.0 |
| Benzyl alcohol | 0.5 |
| 1-Isopropyl-2-undecyl-2-imidazoline | 1.0 |
| Polyethylene glycol | 10.0 |
| Isopropyl lanolate | 3.0 |
| Lantrol | 1.0 |
| Acetylated lanolin | 0.5 |

-continued

| | % |
|---|---|
| C$_{12}$–C$_{15}$ benzoate | 5.0 |
| Diisopropyl adipate | 2.0 |
| Cetyl alcohol | 1.0 |
| Veegum | 1.0 |
| Propylene glycol | 3.0 |
| Purified water | 70.0 |

EXAMPLE 55

The following antineoplastic solution is prepared:

| | % |
|---|---|
| 5-fluorouracil | 5% |
| 1-Isopropyl-2-undecyl-2-imidazoline | 1.5% |
| Polyethylene glycol | 5% |
| Purified water | 88.5% |

EXAMPLE 56

The following insect repellant atomizing spray is prepared:

| | % |
|---|---|
| N,N—diethyltoluamide | 0.5 |
| 1-Isopropyl-2-undecyl-2-imidazoline | 0.5 |
| Ethanol | 99 |

EXAMPLE 57

The following cream formulation may be prepared containing about 0.001 to 1 percent, with preferably 0.1% fluocinolone acetonide:

| | % |
|---|---|
| Oil Phase | |
| Fluocinolone acetonide | 0.1 |
| 1-Isopropyl-2-undecyl-2-imidazoline | 1.6 |
| Cetyl alcohol | 9.3 |
| Stearyl alcohol | 1.3 |
| Glyceryl monostearate | 3.8 |
| Water Phase | |
| Propylene glycol | 10 |
| Sodium dodecyl sulfate | 0.1 |
| Deionized water q.s. | 100 |

The steroid is dissolved in the vehicle and added to a stirred, cooling melt of the other ingredients. The preparation is particularly useful for the treatment of inflamed dermatoses by topical application to the affected skin area. The amount and frequency of application is in accordance with standard practice for topical application of this steroid. Penetration of this steroid in the inflamed tissue is enhanced and a therapeutic level is achieved more rapidly and sustained for longer duration than when the steroid is applied in the conventional formulation.

EXAMPLE 58

The following analgesic gel is prepared:

| | % |
|---|---|
| Carbopol 941 | 1.5 |

-continued

|  | % |
| --- | --- |
| Indomethacin | 1 |
| Ethanol | 35 |
| Diisopropanolamine | 1.8 |
| Diisopropyl adipate | 5 |
| 1-Isopropyl-2-undecyl-2-imidazoline | 2 |
| Water | 53.7 |

EXAMPLE 59

The following cream formulation is prepared:

|  | % |
| --- | --- |
| Isosorbide dinitrate | 10 |
| Glycerol monostearate | 5.5 |
| Polyoxyethylene stearate | 4.5 |
| $C_8$–$C_{18}$ fatty acid esters of a glycerol ethoxylated with about 7 moles of ethylene oxide | 8 |
| 1-Isopropyl-2-undecyl 2-imidazole | 2 |
| Sorbic acid | 0.165 |
| Ascorbyl palmitate | 0.055 |
| Citric acid | 0.1 |
| Na EDTA | 0.014 |
| Fragrance | 0.05 |
| Water | 69.616 |

This formulation is effective in the treatment of angina.

EXAMPLE 60

The following skin moisturizing formulation is prepared:

|  | % |
| --- | --- |
| Pyrrolidonecarboxylic acid Na | 1 |
| Glycerine | 4 |
| Citric acid | 0.03 |
| Sodium citrate | 0.05 |
| Allantoin | 0.1 |
| Ethanol, 95% | 9 |
| Oleth-15 | 1 |
| Linoleic acid | 1 |
| 1-isopropyl-2-undecyl-2-imidazoline | 2 |
| Sunscreen agent | 0.1 |
| Water | 81.72 |

EXAMPLE 61

Examples 49–60 are repeated, except the 1-isopropyl-2-undecyl-2-imidazoline is replaced with an equal amount of each of the following listed compounds, and comparable results are obtained.
4-trifluoromethyl-2-undecyl-2-oxazoline
4-Methyl-4-trifluoromethyl-2-undecyl-2-oxazoline
4,4-Dimethyl-2-(1-dodecen-2-yl)-2-oxazoline
4-t-Butyl-2-(dodecyl)-2-oxazoline
4,4-Dimethyl-2-(2-dodecyl)-2-oxazoline
2-(Methyl-2-decyl)-2-oxazoline
4,4-Dimethyl-2-(2-methyl-2-decyl)-2-oxazoline
2-Undecyl-2-imidazoline
1-Isopropyl-2-pentyl-2-imidazoline
1-Methyl-2-heptyl-2-imidazoline
1-Hydroxyethyl-2-octyl-2-imidazoline
4-Methyl-2-undecyl-2-imidazoline
4,4-Dimethyl-2-undecyl-2-imidazoline
4-Methyl-4-t-butyl-2-undecyl-2-imidazoline
4,4-Dimethyl-1-isopropyl-2-pentyl-2-imidazoline
4,4-Dimethyl-1-isopropyl-2-undecyl-2-imidazoline
1-Isopropyl-2-(2-dodecyl)-2-imidazoline
4,4-Dimethyl-2-(2-dodecyl)-2-imidazoline
4,4-Dimethyl-1-isopropyl-2-(2-dodecyl)-2-imidazoline
2-(2-Methyl-2-decyl)-2-imidazoline
4,4-Dimethyl-2-(2-methyl-2-decyl)-2-imidazoline
4,4-Dimethyl-1-isopropyl-2-(2-methyl-2-decyl)-2imidazoline
1-[2-(Trimethylacetoxy)ethyl]-2-octyl-2-imidazoline The next preceding list of compounds, along with 1-isopropyl-2-undecyl-2-imidazoline have been found to be significantly superior penetration enhancing agents, both as compared with the prior art and as compared with the other examples given herein.

While particular embodiments of the invention have been described it will be understood of course that the invention is not limited thereto since many obvious modifications can be made and it is intended to include within this invention any such modifications as will fall within the scope of appended claims.

Industrial Application

This invention is useful in the pharmaceutical and agricultural industries and in the preparation of compositions for cosmetic, diagnostic and therapeutic use.

What is claimed is:

1. The method for topically administering fluocinolone acetonide to the skin of humans and animals for localized use comprising applying to such skin or membrane a mixture of fluocinolone acetonide and a amount of penetration enhancing compound having the structural formula:

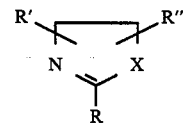

wherein: R is a saturated or unsaturated hydrocarbon group with from 5 to 19 carbon atoms; R' and R" are hydrogen, lower alkyl, trifluoromethyl, lower hydroxyalkyl or lower alkyl ester of lower hydroxyalkyl, with the proviso that both R' and R" are not lower hydroxyalkyl; X is O or NR; R, being hydrogen, lower alkyl, lower alkenyl, lower hydroxyalkyl or lower alky ester of lower hydroxyalkyl.

2. The method for topically administering one or more physiologically active agents at least one of which is a steroid to the skin humans and animals for localized use comprising applying to such skin or membrane a mixture of fluocinolone acetonide and a amount of penetration enhancing compound having the structural formula:

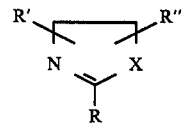

wherein: R is a saturated or unsaturated hydrocarbon group with from 5 to 19 carbon atoms; R' and R" are hydrogen, lower alkyl trifluoromethyl, lower hydroxyalkyl or lower alkyl ester of lower hydroxyalkyl, with the proviso that both R' and R" are not lower hydroxyalkyl; X is O or NR; $R_1$ being hydrogen, lower alkyl, lower alkenyl, lower hydroxyalkyl or low alkyl ester of lower hydroxyalkyl.

3. A composition useful for topically administering physiologically active agents through the skin and mucous membranes of humans and animals in a transdermal device or formulation for systemic use or to the skin of humans and animals for localized use comprising:

(a) an effective amount of one or more physiologically active agents at least one of which is a steroid, and (b) a non-toxic, effective penetrating amount of a penetrationenhancing compound of formula:

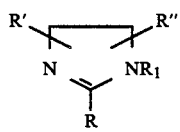

wherein: R is a saturated or unsaturated hydrocarbon group with from 5 to 19 carbon atoms; R' and R" are hydrogen, lower alkyl, trifluoromethyl, lower hydroxyalkyl or lower alkyl ester of lower hydroxyalkyl, with the proviso that both R' and R" are not lower hydroxyalkyl; $R_1$ being hydrogen, lower alkyl, lower alkenyl, lower hydroxyalkyl or lower alkyl ester of lower hydroxyalkyl 4. The composition of claim 3 wherein at least one steroid is fluocinolone.

5. A method for topically administering physiologically active agents through the skins and mucous membranes of humans and animals in a transdermal device or formulation for systemic use or to the skin of humans and animals for localized use, the improvement comprising applying to such skin or membrane a mixture of at least one physiologically active agent, at least one of which is a steroid, and a non-toxic, effective penetrating amount of penetration-enhancing compound having the structural formula:

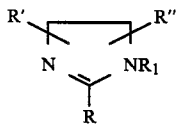

wherein: R is a saturated or unsaturated hydrocarbon group with from 5 to 19 carbon atoms; R' and R" are hydrogen, lower alkyl, trifluoromethyl, lower hydroxyalkyl or lower alkyl ester of lower hydroxyalkyl, with the proviso that both R' and R" are not lower hydroxyalkyl; R, being hydrogen, lower alkyl, lower alkenyl, lower hydroxyalkyl or lower alkyl ester of lower hydroxyalkyl.

6. The composition of claim 5 wherein the at least one steroid is fluocinolone.

7. A composition useful for topically administering physiologically active agents through the skin and mucous membranes of humans and animals in a transdermal device or formulation for systemic use or to the skin of humans and animals for localized use comprising:

(a) an effective amount of one or more physiologically active agents at least one of which is a steroid, and (b) a non-toxic, effective penetrating amount of a penetration enhancing compound of formula:

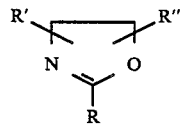

wherein: R is a saturated or unsaturated hydrocarbon group with from 5 to 19 carbon atoms; R' and R" are hydrogen, lower alkyl, trifluoromethyl, lower hydroxyalkyl or lower alkyl ester of lower hydroxyalkyl, with the proviso that both R' and R" are not lower hydroxyalkyl.

8. The composition of claim 7 wherein at least one steroid is fluocinolone.

9. A method of topically administering physiologically active agents through the skins and mucous membranes of humans and animals in a transdermal device or formulation for systemic use or to the skin of humans and animals for localized use, the improvement comprising applying to such skin or membrane a mixture of one or more physiologically active agents at least one of which is a steroid and a non-toxic, effective penetrating amount of penetration-enhancing compound having the structural formula:

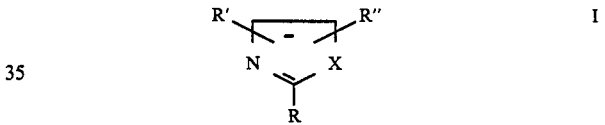

wherein: R is a saturated or unsaturated hydrocarbon group with from 5 to 19 carbon atoms; R' and R" are hydrogen, lower alkyl, trifluoromethyl, lower hydroxyalkyl or lower alkyl ester of lower hydroxyalkyl, with the proviso that both R' and R" are not lower hydroxyalkyl.

10. The composition of claim 8 wherein at least one steroid is fluocinolone.

11. The method of claim 2 wherein at least one steroid is fluocinolone acetonide and wherein the penetration enhancing compound is selected from the group consisting of 4-methyl-2(2-dodecyl)2-oxazoline, 4-isopropyl-2-(2-dodecyl)-2-oxazoline, 4-trifluoromethyl-2(2-dodecyl)-2-oxazoline, 4-isopropyl-2-(2-methyl-2-dodecyl)-2-oxazoline, 4-Methyl-2-undecyl-2-imidazoline, 4-isopropyl-2-undecyl-2-imidazoline, 4-t-butyl-2-undecyl-2-imidazoline, 4-trifluoromethyl-2-undecyl-2-imidazoline, 1,4-diisopropyl-2-undecyl-2-imidazoline, 4-methyl-1-isopropyl-2-undecyl-2-imidazoline, 4-methyl-2-(2-dodecyl)-2-imidazoline, and 4-Methyl-2-(2-methyl-2-decyl)-2-imidazoline, 4,4-dimethyl-2-undecyl-2-oxazoline, 4 methyl-4-trifluoro-methyl-2-undecyl-2oxazoline, 4,4-dimethyl-2-(1-dodecen-2-yl)-2-oxazoline, 4methyl-4-trifluoromethyl-2-(1-dodecen-2-yl)-2-oxazoline, 4,4-dimethyl-2-(2-dodecyl)-2-oxazoline, 4,4-dimethyl-2-(2-methyl-2-decyl)-2-oxazoline, 4,4dimethyl-2-undecyl-2-2imidazoline, 4-methyl-4-t-butyl-2-undecyl-2-imidazoline, 4,4-dimethyl-1-isopropyl-2-undecyl-2-imidazoline, 4-methyl-1,4-diisopropyl-2-undecyl-2imidazoline, 4,4-dimethyl-2-(2-dodecyl)-2-imidazoline, 4,4-dimethyl-1-isopropyl-2-(2-dodecyl)-2-imidazoline, 4,4-dimethyl-2(2-methyl-2-decyl)-2-imidazoline, 4,4-dimethyl-1-isopropyl-2(2-methyl-2-decyl)-2-imidazoline, 4-hydroxymethyl-4-methyl-2-undecyl-2-oxazoline, 4-hydroxymethyl-4-trifluoromethyl-2-undecyl-2-oxazoline, 4-trimethylacetoxymethyl-4-methyl-2-undecyl-2-oxazoline, 4-hydroxymethyl-4-methyl-2-(2-dodecyl)-2-oxazoline, 4-hydroxylmethyl-4-methyl-2-(2-decyl)-2-oxazoline, 4-trimethylacetoxymethyl-4-methyl-2-(2-dodecyl)-2-oxazoline, and 4-trimethylacetoxymethyl-4-methyl-2-(2-methyl-2-decyl)-2-oxazoline, 4-methyl-2-nonyl-2-oxazoline, 4-methyl-2-undecyl-2-oxazoline, 4-trifluoromethyl-2-undecyl-2-oxazoline, 4-isopropyl-2-nonyl-2-oxazoline, 4-isopropyl-2-undecyl-2-oxazoline, 4-t-butyl-2-undecyl-2-oxazoline, 4-methyl-4-trifluoromethyl-2-undecyl-2-oxazoline, 4-methyl-4-isopropyl-2-undecyl-2-oxazoline, 4-methyl-4-t-butyl-2-undecyl-2-oxazoline, 4-trifluoromethyl-2-(1-dodecen-2-yl)-2-oxazoline, 4-methyl-4-trifluoromethyl-2-(1-dodecen-2-yl)-2-oxazoline, 4-hydroxymethyl-4-ethyl-2-undecyl-2-oxazoline, 4-hydroxymethyl-4-trifluoromethyl-2-undecyl-2-oxazoline, 4-trimethylacetoxymethyl-4-methyl-2-undecyl-2-oxazoline, 2-(2-decyl)-2-oxazoline, 2-(2-dodecyl)-2-oxazoline, 4-methyl-2-(2-dodecyl)-2-oxazoline, 4-isopropyl-2-(2-dodecyl)-2-oxazoline, 4-t-butyl-2-(2-dodecyl)-2-oxazoline, 4-trifluoromethyl-2-(2-dodecyl)-2oxazoline, 4,4-dimethyl-2-(2-dodceyl)-2-oxazoline, 4-methyl-4-isopropyl-2-(2-dodecyl)-2-oxazoline, 4-methyl-4-t-butyl-2-(2-dodecyl)-2-oxazoline, 4-methyl-4-trifluoromethyl-2-(2-dodecyl)-2-oxazoline, 4-hydroxymethyl-4-methyl-2-(2-dodecyl)-2-oxazoline, 4-2[2-(trimethylacetoxy)ethyl]-4-methyl-2-(2-dodecyl)-2-oxazoline, 2(2-methyl-2-decyl)-2-oxazoline, 2-(2-methyl)-2-dodecyl)-2-oxazoline, 4-trifluoromethyl-2-(2-methyl-2-decyl)-2-oxazoline, 4,4-dimethyl-2-(2-methyl-2-decyl)-2-oxazoline, 4,4-dimethyl-2-(2-methyl-3-tridecyl)-2-oxazoline, 1-isopropyl-2-pentyl-2-imidazoline, 1-hydroxyethyl-2-octyl-2-imidazoline, 1-[2-(trimethylacetoxy)ethyl]-2-octyl-2-imidazoline, 4-methyl-2-undecyl-2-imidazoline, 4-isopropyl-2-undecyl-2-imidazoline, 4-t-butyl-2-undecyl-2-imidazoline, 4-trifluoromethyl-2-undecyl-imidazoline, 1,4-diisopropyl-2-undecyl-2-imidazoline, 4-t-butyl-1-isopropyl-2-undecyl-2-imidazoline, 4,4-dimethyl-2-nonyl-2-imidazoline, 4,4-dimethyl-2-undecyl-2-imidazoline, 4-methyl-4-isopropyl-2-undecyl-2-imidazoline, 4-methyl-4-t-butyl-2-undecyl-2-imidazoline, 4,4-diisopropyl-2-undecyl-2-imidazoline, 4-methyl-4-trifluoromethyl-2-undecyl-2-imidazoline, 4,4-dimethyl-1-isopropyl-2-pentyl-2-imidazoline, 4,4-dimethyl-2-isopropyl-2-undecyl-2-imidazoline, 4,4-dimethyl-1-isopropyl-2-tridecyl-2imidazoline, 4-4-dimethyl-1-isopropyl-2-pentadecyl-2-imidazoline,4,4-dimethyl-1-isopropyl-2-heptadecyl-2-imidazoline, 4,4-dimethyl-1-n-butyl-2-heptadecyl-2imidazoline, 4,4-dimethyl-1-s-butyl-2-heptadecyl-2-imidazoline, 4-methyl-1,4-diisopropyl-2-undecyl-2imidazoline, 4-methyl-4-t-butyl-1-isopropyl-2-undecyl-imidazoline, 1,4,4-triisopropyl-2-undecyl-2-imidazoline, 4,4-dimethyl-1-hydroxyethyl-2-undecyl-2-imidazoline, 4,4-dimethyl-1-hydroxyethyl-2heptadecyl-2-imidazoline, 4,4-dimethyl-1 -2-undecyl-2-imidazoline, 4,4-dimethyl-1-(1-hydroxy-2-methyl-2-propyl)-2-undecyl-2-imidazoline, 4,4-dimethyl-1-(1-acetoxy-2-methyl-2-propyl)-2-undecyl-2-imidazoline, 2-(2-decyl)-2-imidazoline, 2(2-dodecyl)-2-imidazoline, 1-hydroxymethyl-2-(2-dodecyl)-2-imidazoline, 1-[2-(trimethylacetoxy)ethyl]-2-(2-dodecyl)-2-imidazoline, 1-isopropyl-2-(2-dodecyl)-2-imidazoline, 4,4-dimethyl-2-(2-dodecyl-2-imidazoline, 4,4-dimethyl-1-isopropyl-2-(2-dodecyl)-2-imidazoline, 2-(1-dodecene-2-yl)-2-imidazoline,1-isopropyl-2-(1-dodecen-2-yl)-2-imidazoline, 4,4-dimethyl-2-(1-dodecen-2-yl)-2-imidazoline, 4,4-dimethyl-1-isopropyl-2-(1-dodecen-2-yl)-2-imidazoline, 2-(2-methyl-2-decyl)-2-imidazoline. 2-(2-methyl-2-dodecyl)-2-imidazoline, 1-hydroxyethyl-2-(2-methyl-2-decyl)-2-imidazoline, 1-trimethylacetoxyethyl-2-(2-methyl-2-decyl)-2-imidazoline, 4,4-dimethyl-2-(2-methyl-2-decyl)-2-imidazoline, 4,4-dimethyl-1-isopropyl-2-(2-methyl-2-decyl)-2-imdazoline, 4,4-dimethyl-1-hydroxyethyl-2-(2-methyl-2-decyl)-2imidazoline, 4,4-dimethyl-1 -2-(2-methyl-2-decyl)-2-imidazoline, and 4,4-dimethyl-1-(1-hydroxy-2-methyl-2-propyl)-2-undecyl-2-imidazoline.

* * * * *